United States Patent [19]

Wuest et al.

[11] Patent Number: 4,927,946

[45] Date of Patent: May 22, 1990

[54] PROCESS FOR THE PREPARATION OF 5-BROMO-5-NITRO-1,3-DIOXANE

[75] Inventors: Willi Wuest, Ratingen; Rainer Eskuchen, Duesseldorf; Herbert Esser, Troisdorf; Hasso Leischner, Duesseldorf, all of Fed. Rep. of Germany

[73] Assignee: Henkel Kommanditgesellschaft auf Aktien, Duesseldorf, Fed. Rep. of Germany

[21] Appl. No.: 345,918

[22] Filed: May 1, 1989

[30] Foreign Application Priority Data

Apr. 30, 1988 [DE] Fed. Rep. of Germany ....... 3814774

[51] Int. Cl.$^5$ ............................................ C07D 319/06
[52] U.S. Cl. ..................................... 549/371; 568/712
[58] Field of Search ................. 549/371; 568/844, 712

[56] References Cited

U.S. PATENT DOCUMENTS

| 3,658,921 | 4/1972 | Wessendorf | 568/712 |
| 3,711,561 | 1/1973 | Wessendorf | 568/712 |
| 3,772,443 | 11/1973 | Wessendorf et al. | 514/452 |
| 3,931,233 | 1/1976 | Conrad | 549/371 |
| 4,754,079 | 6/1988 | Bison et al. | 568/712 |

FOREIGN PATENT DOCUMENTS 2913466 10/1980 Fed. Rep. of Germany .

OTHER PUBLICATIONS

Chemical Abstracts, vol. 105:191101c; Chapter 28—Heterocycles, p. 731; 5-Bromo-5-Nitro-1,3-Dioxanes; Nov. 24, 1986.

Chemical Abstracts, vol. 102:100612u; Chapter 62—Essential Oils and Cosmetics; p. 299; Organic Synthesis, Antibacterial Evaluation, and Quantitative Structure-Activity Relationships (QSCR) of Cosmetic Preservatives Relates to 5-Bromo-5-Nitro-1,3-Dioxane; Mar. 25, 1985.

*Primary Examiner*—Nicky Chan
*Attorney, Agent, or Firm*—Ernest G. Szoke; Wayne C. Jaeschke; Henry E. Millson, Jr.

[57] ABSTRACT

Unpurified 2-bromo-2-nitro-1,3-propanediol is used as the starting material for a process for the preparation of 5-bromo-5-nitro-1,3-dioxane from 2-nitro-1,3-propanediol without the use of an organic solvent on an industrial scale. This is carried out in such a way that in a first stage a mixture of bromine and aqueous hydrogen bromide solution is cooled and an aqueous solution of an alkali metal or an alkaline-earth metal salt of 2-nitro-1,3-propanediol is added at such a rate that, with cooling, the maximum reaction temperature does not exceed 30° C., and then in a second reaction stage paraformaldehyde and sulfuric acid are added, left to react above room temperature, and the organic phase separated.

16 Claims, No Drawings

PROCESS FOR THE PREPARATION OF 5-BROMO-5-NITRO-1,3-DIOXANE

BACKGROUND OF THE INVENTION

1. Field of the Invention:

This invention relates to an improved process for the preparation of the microbiocidally active substance, 5-bromo-5-nitro-1,3-dioxane.

2. Statement of Related Art:

5-Bromo-5-nitro-3-dioxane is known from German patent applications DE-B No. 19 66 920 and DE-C No. 22 63 206. Processes for its preparation are also set forth in these applications. According to the examples in DE-B No. 19 66 920, in one example benzene or methylene chloride is used as solvent, while in the other examples sublimation conditions are used in a sublimation apparatus. The process of DE No. 22 63 206 uses the solvent ethylene chloride.

DESCRIPTION OF THE INVENTION

Other than in the operating examples, or where otherwise indicated, all numbers expressing quantities of ingredients or reaction conditions used herein are to be understood as modified in all instances by the term "about".

Against the background of the above prior art, a process is needed which enables 5-bromo-5-nitro-1,3-dioxane to be prepared on an industrial scale without the use of an organic solvent even when using crude, unpurified 2-bromo-2-nitro-1,3-propanediol.

The present invention relates to a two-stage process for the preparation of 5-bromo-5-nitro-1,3-dioxane from 2-nitro-1,3-propanediol. In the first stage to a mixture of bromine and aqueous hydrogen bromide solution is added with cooling an aqueous solution of an alkali metal and/or a water-soluble alkaline-earth metal salt of 2-nitro-1,3propanediol at a rate such that the reaction temperature does not exceed 30° C. Thereafter, in a second reaction stage paraformaldehyde and sulfuric acid are added to the reaction mixture from the first stage, and the resulting mixture is allowed to react completely at a temperature above room temperature, followed by separation of the organic phase.

In carrying out the first stage:

As the mixture of bromine and hydrogen bromide solution there can be employed mixtures of bromine with an aqueous hydrogen bromide solution of 50 to 62 % by weight HBr, and preferably azeotropically distilled aqueous HBr-solution. The proportions (molar) of HBr to bromine in the mixtures range from 1:3 to 1:10, preferably 1:5 to 1:5.5, and more preferably 1:5.3.

Into the above mixture of bromine and aqueous hydrogen bromide there is added at a controlled rate an alkali metal salt (e.g. the potassium or sodium salt) and/or, provided it is water-soluble, an alkaline-earth metal salt (e.g. the calcium salt) of 2-nitro-1,3-propanediol.

According to a preferred procedure for the process of the invention, the potassium salt of 2-nitro-1,3-propanediol is used herein.

To enable the first stage of the process of the invention to be carried out with better space-time consumption, the alkali metal salt and/or alkaline-earth metal salt is preferably used in a 40 to 60% by weight aqueous solution or suspension.

The reaction heat evolved when the salt is added at a controlled rate, e.g. dropwise, into the mixture of bromine and hydrogen bromide solution is dissipated by use of external cooling, e.g. in a heat-exchanger. For this purpose plate heat-exchangers or preferably tube-bundle heat-exchangers can be employed. Heat-exchangers of other constructions can also be used, but it is generally true that as the exchange area decreases the rate of addition must also be decreased, because a temperature of 30° C. should not be exceeded during the reaction.

According to a preferred embodiment of the first stage of the process, the mixture of bromine and hydrogen bromide solution is formed in an agitator vessel made of corrosion-resistant material, for example tantalum, and pumped by means of a centrifugal pump through a corrosion-resistant tubular reactor into a tube-bundle heat-exchanger and returned from there into the agitator vessel. The reaction mixture is pumped through the system until the whole solution of nitro-alcohol salt has been introduced.

According to a preferred procedure should any bromine still be present at the end of the first stage reaction, shown by coloration of the solution, this can be reduced by the addition of a reducing agent, e.g. aqueous hydroxylamine solution. The hydroxylamine solution is added gradually in drops until the reaction product is at least substantially de-colorized.

In carrying out the second stage:

The aqueous reaction mixture containing bromides and 2-bromo-2-nitro-1,3-propanediol obtained in the first stage can be introduced directly into the second stage. Paraformaldehyde is first added to the mixture. The molar ratio of paraformaldehyde to the 2-bromo-2-nitro-1,3-propanediol is preferably 1:1 to 1.3:1, and more preferably 1.1:1.

So as to accelerate the cyclization reaction sulfuric acid is then added, preferably 96 to 98% sulfuric acid. The molar ratio of 2-bromo-2-nitro-1,3-propanediol to sulfuric acid should be between 1:1 and 1:5, preferably between 1:2.5 and 1:3.5.

It has been found advantageous to add the paraformaldehyde to the reaction mixture before adding the sulfuric acid thereto.

The cyclization reaction is advantageously carried out at temperatures above room temperature. In order to attain these temperatures, it is preferable to introduce the sulfuric acid to the reaction mixture so that temperatures of 70° to 110° C., and preferably 90° to 100° C., are reached. The reaction mixture is allowed to remain at these temperatures for between a few minutes and 2 hours while being stirred for thorough mixing. The reaction vessel is desirably fitted with a reflux condenser and the reaction mixture is allowed to boil under reflux. At the end of the reaction the stirrer is stopped and the organic phase, which consists predominantly of 5-bromo-5-nitro-1,3-dioxane, is separated from the salt solution. It is preferable that the reaction temperature is not allowed to drop below 70° C., since at lower temperatures the organic phase has a tendency to crystallize.

While the present invention is not limited by the reaction mechanism, it is assumed that the salts (for example potassium bromide) formed in the first stage yield hydrogen bromide after the addition of sulfuric acid, and that the latter as a strong acid catalyzes the reaction, while the sulfuric acid excess functions to take up water of reaction. It has been found that higher excesses of sulfuric acid are to be avoided because then, under the reaction conditions, oxidation reactions and thus a decrease in the yield results.

The invention will be illustrated but not limited by the following examples.

EXAMPLES

Example 1

A. Preparation of 2-nitro-1,3-propanediol potassium salt. The process was carried out in a pilot plant, consisting of a 0.8 m$^3$ agitator vessel, a centrifugal pump with a throughput rate of 25 m$^3$.h$^{-1}$; H=40 m, and a 12 m$^2$ plate heat-exchanger.

229.2 kg of 37% by weight of aqueous formaldehyde solution was placed in the agitator vessel, and by pumping the solution over the heat-exchanger and back into the agitator vessel, the solution was cooled to a temperature of 0° to 10° C. Then over the course of 30 minutes, 201.4 kg of a 45% by weight aqueous potash lye was added over 30 minutes; mixing took place in the turbulence of the centrifugal pump. The temperature of the mixture was held between 0° and 10° C.

82.1 kg of nitromethane was added to this mixture over 2 hours. The rate of addition was adjusted so that the temperature of the reaction mixture did not exceed 15° C. The temperature was regulated in part by the rate of addition of the nitromethane. The post-reaction time was 15 minutes, and during this time the reaction mixture was pumped around the circuit. At the end of the reaction time the residual content of nitromethane had fallen to under 1% by weight. The potassium salt of the 2-nitro-1,3-propanediol which was formed, remained in solution at temperatures down to −15° C.

B. Bromination of 2-nitro-1,3-propanediol potassium salt to 2-bromo-2-nitro-1,3-propanediol. The bromination was carried out in an enamelled agitator vessel with a volume of 1.3 m$^3$. This was connected via a pipe to a centrifugal pump with a throughput rate of 10 m$^3$/h, H=12 m, to a 6 cm tube-bundle heat-exchanger. The heat-exchanger outlet was in turn connected back to the agitator vessel. 228.3 kg of bromine from a bromine storage container and 35.1 kg of 62% aqueous HBr from another storage container were introduced into the agitator and pumped through the product-cooling cycle. Then in the course of 1.5 hours 512.7 kg of the reaction mixture from step A. above (the reaction mixture containing the potassium salt of 2-nitro-1,3-propanediol) was added. The reaction temperature was kept below 30° C. during the entire reaction period; when the reaction temperature reached 30° C. the rate of addition of the potassium salt solution was reduced. After the addition was completed and following a post-reaction period of 0.5 hours the excess bromine was reduced with 14.8 kg of a 40% by weight aqueous hydroxylammonium chloride solution over the course of 0.25 hour.

Example 2

The acetalization of 2-bromo-2-nitro-1,3-propanediol was carried out in a 1.3 m$^3$ agitator vessel. First 42.2 kg of paraformaldehyde was added to the 790.9 kg of the reaction mixture obtained in Example 1 in the preparation of 2-bromo-2-nitro-1,3-propanediol. Then 365.9 kg of 96% sulfuric acid was added at such a rate that the reaction mixture heated up to 90° to 100° C. After completion of the addition of the sulfuric acid the reaction mixture was kept boiling under reflux at 90° to 100°πC. After completion of the acetalization the reaction mixture was cooled down to 70° C. A two-phase system was formed. The water soluble salts were present in the aqueous upper phase, and crude 5-bromo-5-nitro-1,3-dioxane was present in the lower organic phase.

To increase the yield, the 953.2 kg of the aqueous upper phase was neutralized with 521.4 kg of 50% sodium hydroxide solution to a pH value of 8, whereupon a further quantity of 5-bromo-5-nitro-1,3-dioxane formed as a lower phase.

For further purification of the crude 5-bromo-5-nitropropanediol, it was washed with 63 kg of a 9% sodium bicarbonate solution and with 170 kg of water (at temperatures of 70° C.). 1,2-Propanediol was recovered and was suitable for re-crystallization. 247.9 kg of pure 5-bromo-5-nitro-1,3-dioxane were obtained.

We claim:

1. A process for the preparation of 5-bromo-5-nitro-1,3-dioxane comprising the steps of
   A. brominating an alkali metal salt and/or a water-soluble alkaline-earth metal salt of 2-nitro-1,3-propanediol by adding said salt to a mixture of bromine and aqueous hydrobromic acid while controlling the temperature of the reaction mixture so that it does not exceed about 30° C. by both cooling the reaction mixture and controlling the rate of addition of said salt to form a reaction mixture containing 2-bromo-2-nitro-1,3-propanediol;
   B. adding to the reaction mixture containing 2-bromo-2 nitro-1,3-propanediol from step A. paraformaldehyde and sulfuric acid and carrying out the reaction at a temperature in the range of from about 70° C. to about 110° C. to form a reaction mixture containing 5-bromo-5-nitro-1,3-dioxane;
   C. allowing the reaction mixture from step B. to separate into an aqueous phase and an organic phase which contains 5-bromo-nitro-1,3-dioxane; and
   D. separating the organic phase from the aqueous phase.

2. The process of claim 1 wherein in step B. the molar ratio of 2-bromo-2-nitro-1,3-propanediol to para-formaldehyde, calculated as formaldehyde, is from about 1:1 to about 1:1.3.

3. The process of claim 2 wherein said molar ratio is about 1:1.1.

4. The process of claim 1 wherein in step B. the molar ratio of 2-bromo-2-nitro-1,-3-propanediol to sulfuric acid is from about 1:1 to about 1:5.

5. The process of claim 4 wherein said molar ratio is from about 1:2.5 to about 1:3.5.

6. The process of claim 2 wherein in step B. the molar ratio of 2-bromo-2-nitro-1,3-propanediol to sulfuric acid is from about 1:1 to about 1:5.

7. The process of claim 3 wherein in step B. the molar ratio of 2-bromo-2-nitro-1,3-propanediol to sulfuric acid is from about 1:2.5 to about 1:3.5.

8. The process of claim 1 wherein in step B. the paraformaldehyde is added prior to the addition of the sulfuric acid.

9. The process of claim 1 wherein in step B. the temperature is in the range of from about 90° C. to about 100° C.

10. The process of claim 1 wherein steps C. and D. are carried out at a temperature above about 70° C.

11. The process of claim 1 wherein in step A. the aqueous hydrobromic acid has a hydrobromic acid content of from about 50 to about 62% by weight.

12. The process of claim 11 wherein in step A. in the mixture of bromine and aqueous hydrobromic acid the molar ratio of hydrobromic acid to bromine is from about 1:3 to about 1:10.

13. The process of claim 12 wherein in step A. said molar ratio is from about 1:5 to about 1:5.5.

14. The process of claim 1 wherein in step A. the salt of 2-nitro-1,3-propanediol is in the form of an aqueous solution containing from about 40 to about 60% by weight of salt.

15. The process of claim 1 wherein the reaction mixture of step A. prior to use in step B. is treated with hydroxylamine until the reaction mixture is substantially colorless.

16. The process of claim 1 wherein process steps A. and B. are both carried out with continuous mixing of the reaction mixtures.

* * * * *